United States Patent [19]
Urbahns et al.

[11] Patent Number: 5,874,462
[45] Date of Patent: Feb. 23, 1999

[54] USE OF SUBSTITUTED 6-AMINO-4H-PYRANS

[75] Inventors: Klaus Urbahns, Wuppertal; Hans-Georg Heine, Krefeld; Bodo Junge; Rudolf Schohe-Loop, both of Wuppertal; Henning Sommermeyer, Köln; Thomas Glaser, Overath; Reilinde Wittka, Köln; Jean-Marie-Viktor de Vry, Rösrath, all of Germany

[73] Assignee: Bayer Aktiengesellschaft, Leverkusen, Germany

[21] Appl. No.: 793,068

[22] PCT Filed: Aug. 10, 1995

[86] PCT No.: PCT/EP95/03168

§ 371 Date: Feb. 14, 1997

§ 102(e) Date: Feb. 14, 1997

[87] PCT Pub. No.: WO96/06091

PCT Pub. Date: Feb. 29, 1996

[30] Foreign Application Priority Data

Aug. 23, 1994 [DE] Germany ............... 44 29 786.6

[51] Int. Cl.$^6$ .......... A61K 31/35; A61K 31/44; C07D 309/32; C07D 405/04
[52] U.S. Cl. ........ 514/459; 549/424; 546/282.1; 514/336
[58] Field of Search ............... 549/424; 514/459

[56] References Cited

U.S. PATENT DOCUMENTS 3,981,893  9/1976  Meyer et al. ............... 260/345.8
4,622,332  11/1986  Wehinger et al. ............... 514/356

OTHER PUBLICATIONS

Tetrahedron Letters No. 21, pp. 1835–1836, 1977 "Synthesis of Heterocyclic Compounds".
Pascual et al., Magn.Res.Chem. 23(9), 1985, 793–194.
Tas et al., Neuro.Letters 94, 1988, 279–284.
Abramenko et al., *Simple Methods of Preparing Derivatives of 2–amino–3–cyano–4N–Pyranes,* Nov.Khim.Sredstva Zanshch.Rast., 7–11 (1979) (English Translation of Russian Publication, both of which are submitted herewith).
Soto et al., Heterocycles, vol. 22, No. 1, 1984, pp. 1–6, 1984.
Pascual et al., CA 104:148178, 1986.

*Primary Examiner*—Laura L. Stockton
*Attorney, Agent, or Firm*—Sprung Kramer Schaefer & Briscoe

[57] ABSTRACT

The invention relates to the use of substituted 6-amino-4H-pyrans for the production of medicaments for the treatment of cerebral disorders, in particular of degenerative disorders such as dementia, and also for treatment of depressions and psychoses. New active compounds are prepared by reaction of the corresponding ylidene compounds with malononitrile.

9 Claims, No Drawings

USE OF SUBSTITUTED 6-AMINO-4H-PYRANS

This application is a 371 of PCT/EP95/03168 filed Aug. 10, 1995.

The present invention related to the use of substituted 6-amino-4H-pyrans, some of which are known, as medicaments, new active compounds and a process for their preparation, in particular their use as cerebrally active agents.

2-Amino-3-cyano-4H-pyrans are already known from some publications [cf. for this Magn. Reson. Chem. 23 (9), 793–4, 1985; Nor. Khim. Sredstva Zashch. Rast. 7–11, 1979].

It has now been found that the substituted 6-amino-4H-pyrans of the general formula (I)

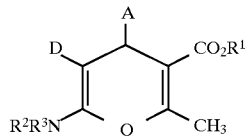

in which

A represents aryl having 6 to 10 carbon atoms or pyridyl, each of which is optionally substituted up to 3 times by identical or different substituents from the group consisting of nitro, cyano, phenyl, halogen and trifluoromethyl or straight-chain or branched alkylthio or alkoxy in each case having up to 6 carbon atoms, $R^1$ represents hydrogen or straight-chain or branched alkyl having up to 8 carbon atoms, $R^2$ and $R^3$ are identical or different and represent hydrogen or straight-chain or branched alkyl or acyl in each case having up to 6 carbon atoms, D represents cyano, nitro or straight-chain or branched alkoxycarbonyl having up to 8 carbon atoms, and their salts surprisingly have a modulating action on potassium channels and are thus suitable for use in the control of cerebral disorders and sickle cell anemia.

In the context of the invention, physiologically acceptable salts are preferred. Physiologically acceptable salts are in general salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid or methanesulphonic acid, ethanesulphonic acid, phenylsulphonic acid, toluenesulphonic acid or naphthalenedisulphonic acid.

The compounds according to the invention can exist in stereoisomeric forms which either behave as image and mirror image (enantiomers), or which do not behave as image and mirror image (diastereomers). The invention relates both to the antipodes and to the racemic forms as well as the diastereomer mixtures. Like the diastereomers, the racemic forms can also be separated into the stereoisomerically uniform constituents in a known manner.

Preferred are those compounds of the general formula (I) in which

A represents phenyl, naphthyl or pyridyl, each of which is optionally substituted up to 3 times by identical or different substituents from the group consisting of nitro, cyano, fluorine, chlorine, bromine, iodine, phenyl and trifluoromethyl or straight-chain or branched alkylthio or alkoxy in each case having up to 4 carbon atoms.

$R^1$ represents hydrogen or straight-chain or branched alkyl having up to 6 carbon atoms, $R^2$ and $R^3$ are identical or different and represent hydrogen or straight-chain or branched alkyl or acyl in each case having up to 4 carbon atoms, D represents cyano or straight-chain or branched alkoxycarbonyl having up to 6 carbon atoms, and their salts, in the control of cerebral disorders.

Particularly preferred are those compounds of the general formula (I) in which

A represents phenyl or pyridyl, each of which is optionally substituted up to 2 times by identical or different substituents from the group consisting of nitro, cyano, fluorine, chlorine, bromine, iodine, trifluoromethyl, methoxy and phenyl or methylthio, D represents cyano, $R^1$ represents hydrogen or straight-chain or branched alkyl having up to 4 carbon atoms, $R^2$ and $R^3$ are identical or different and represent hydrogen or straight-chain or branched alkyl or acyl in each case having up to 3 carbon atoms, and their salts, in the control of cerebral disorders.

The compound of the formula (I) according to the invention show an unforeseeable, useful spectrum of pharmacological action.

They are channel modulators having selectivity for calcium-dependent potassium channel of high conductivity (BK(Ca) channels), in particular of the central nervous system.

On account of their pharmacological properties, they can be employed for the production of medicaments for the treatment of degenerative central nervous system disorders, such as on occurrence of dementias such as multiinfarct dementia (MID), primary degenerative dementia (PDD), presenile and senile dementia in Alzheimer's disease, HIV dementia and other forms of dementia. They are further suitable for the treatment of Parkinson's disease or amyotrophic lateral sclerosis and also multiple sclerosis.

The active compounds are furthermore suitable for the treatment of brain function disorders in old age, of organic brain syndrome (OBS) and of age-related memory disorders (age-associated memory impairment, AAMI).

They are suitable for the prophylaxis and treatment and for the control of the sequelae of cerebral circulatory disorders such as cerebral ischaemias, strokes, craniocerebral traumata and of subarachnoid haemorrhages.

They are useful for the treatment of depressions and psychoses, e.g. schizophrenias. They are additionally suitable for the treatment of disorders of neuroendocrine secretion and of neurotransmitter secretion and health disorders connected therewith such as mania, alcoholism, drug abuse, dependence or abnormal eating behavior. Other application areas are the treatment of migraine, sleep disorders and of neuropathies. They are moreover suitable as analgesics.

The active compounds are further suitable for the treatment of disorders of the immune system, in particular of T-lymphocyte proliferation and for affecting the smooth musculature, in particular of uterus, urinary bladder and bronchial tract and for the treatment of diseases connected therewith such as e.g. asthma and urinary incontinence and for the treatment of high blood pressure, arrhythmia, angina and diabetes.

The invention additionally relates to new compounds of the formula (I)

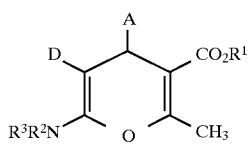

and their salts,
having the substituent meanings indicated in the following table:

| A | D | $R^1$ | $R^2$ | $R^3$ |
|---|---|---|---|---|
| $C_6H_5$ | CN | $CH_3$ | H | H |
| $C_6H_4$-o-$CF_3$ | CN | $CH_3$ | H | H |
| $C_6H_4$-m-$NO_2$ | CN | $CH_3$ | H | H |
| $C_6H_3$-o,m-Cl | CN | $CH_3$ | H | H |
| $C_6H_4$-p-$CF_3$ | CN | $CH_3$ | H | H |
| $C_6H_4$-p-Cl | CN | $CH_3$ | H | H |
| $C_6H_3$-,m-Cl | CN | $CH_3$ | H | H |
| $C_5H_4$-p-$OCH_3$ | CN | $CH_3$ | H | H |
| $C_6H_4$-p-$C_6H_5$ | CN | $CH_3$ | H | H |
| $C_6H_3$-m,p-Cl | CN | $CH_3$ | H | H |

The compounds of the general formula (I) are prepared by [A] in the case where D=cyano reacting compounds of the general formula (II)

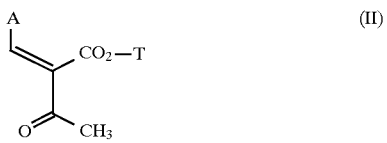

in which
A includes the scope of meaning indicated and
T has the scope of meaning of $R^1$ indicated above, but does not represent hydrogen, with malononitrile, in organic solvents and in the presence of a base, or
[B] reacting compounds of the general formula (II) with compounds of the general formula (III)

in which
D, $R^2$ and $R^3$ have the meaning indicated.
The process can be illustrated by the following equation:

[A]

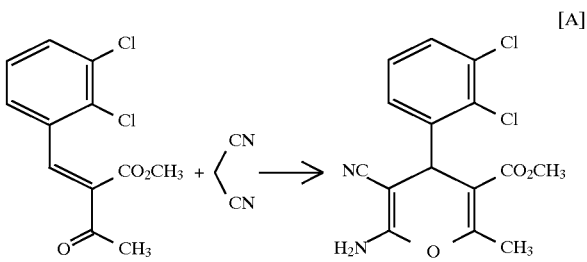

Suitable solvents are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, acetonitrile, or amides such as hexamethylphosphoramide or dimethylformamide, or acetic acid or halogenated hydrocarbons such as methylene chloride or carbon tetrachloride, or hydrocarbons such as benzene or toluene, or pyridine. It is also possible to use mixtures of the solvents mentioned. Methanol is particularly preferred.

Suitable bases are in general alkali metal hydrides or alkoxides, such as, for example, sodium hydride or potassium tert-butoxide, or cyclic amines, such as, for example, piperidine, dimethylaminopyridine or $C_1$–$C_4$-alkylamines, such as, for example, triethylamine. Triethylamine is preferred.

The base is in general employed in an amount from 1 mol to 5 mol, preferably from 1 mol to 2 mol, relative to 1 mol of the compounds of the general formula (II).

The reaction with compounds of the general formula (III) is in general carried out in a temperature range from 0° C. to 150 C., preferably from 40° C. to 80° C.

The reactions can be carried out at normal pressure, but also at elevated or reduced pressure (e.g. 0.5 to 3 bar). In general the reaction is carried out at normal pressure.

Enantiomerically pure forms are obtained e.g. by separating diastereomer mixtures of the compounds of the general formula (I), in which $R^1$ represents an optically active ester radical, by a customary method, then either directly transesterifying or first preparing the chiral carboxylic acids and then preparing the enantiomerically pure compounds by esterification.

The separation of the diastereomers is in general carried out either by fractional crystallization, by column chromatography or by countercurrent distribution. Which is the optimum process must be decided from case to case; sometimes it is also expedient to use combinations of the individual processes. Separation by crystallization or countercurrent distribution or a combination of both processes is particularly suitable.

The enantiomerically pure compounds are also accessible by chromatography of the racemic esters on chiral phases.

$^{86}$Rubidium efflux from C6-BU1 glioma cells

The experiments were carried out with slight modifications according to the method described by Tas et al. (Neurosci. Lett. 94, 279–284, (1988)). To do this, rat C6-BU1 glioma cells are used. From the data obtained by liquid scintillation, the increase in Rb efflux produced by ionomycin above the basal efflux is calculated and set as 100%. The stimulations in the presence of test substances are then related to this value.

The present invention also includes pharmaceutical preparations which, in addition to inert, non-toxic, pharmaceutically suitable auxiliaries and excipients, contain one or more compounds of the general formula (I), or which consist of one or more active compounds of the formula (I), and processes for the production of these preparations.

The active compounds of the formula (I) should be present in these preparations in a concentration from 0.1 to 99.5% by weight, preferably from 0.5 to 95% by weight of the total mixture.

In addition to the active compounds of the formula (I), the pharmaceutical preparations can also contain other pharmaceutical active compounds.

The abovementioned pharmaceutical preparations can be prepared in a customary manner by known methods, for example using the auxiliary(ies) or excipient(s).

In general, it has proven advantageous to administer the active compound(s) of the formula (I) in total amounts from about 0.1 to about 100 mg/kg, preferably in total amounts from about 1 mg/kg to 50 mg/kg of body weight every 24 hours, if appropriate in the form of several individual doses, to achieve the desired result.

However, if appropriate it can be advantageous to depart from the amounts mentioned, namely depending on the nature and on the body weight of the subject treated, on individual behaviour towards the medicament, the nature and severity of the disorder, the type of preparation and administration, and the time or interval at which administration takes place.

Mobile phase mixtures:
a): toluene/ethyl acetate 1:1
b): toluene/ethyl acetate 3:1

PREPARATION EXAMPLES

Example 1
Methyl 6-amino-5cyano-4-(2,3-dichlorophenyl)-2-methyl-4H-pyran-3-carboxylate

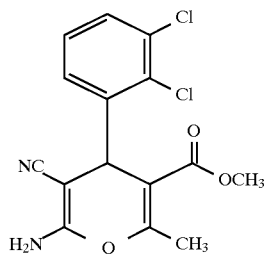

1.8 g (28 mmol) of malononitrile, 7.1 g (25 mmol) of methyl 2-acetyl-3-(2,3-dichlorophenyl)acrylate, 0.3 g (3 mmol) of triethylamine and 0.1 g (2.4 mmol) of glacial acetic acid are heated to reflux in 50 ml of methanol. After 10 min a crystalline precipitate is deposited, 60 ml of methanol are added and the suspension is heated to reflux again. After cooling to room temperature, the precipitate is filtered off with suction and washed with cold methanol. 7.2 g (85%) of m.p. 192–194 are obtained.

The compounds listed in Table 1 are prepared in analogy to the procedure of Example 1:

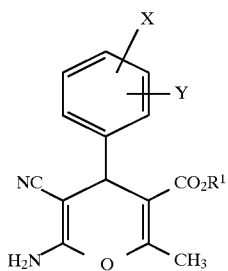

| Ex. No. | X, Y | $R^1$ | Yield (% of theory) | m.p. (°C.) | $R_f$* |
|---|---|---|---|---|---|
| 2 | 2-H, 3-H | $CH_3$ | 15 | 170–4 | 0.46/a |
| 3 | 2-$CF_3$, 3-H | $CH_3$ | 64 | 171–4 | 0.61/a |
| 4 | 3-$NO_2$, 2-H | $CH_3$ | 46 | 195–9 | 0.28/b |
| 5 | 4-$CF_3$, 3-H | $CH_3$ | 57 | 152–5 | 0.49/a |
| 6 | 4-Cl, 3-H | $CH_3$ | 15 | 153–4 | 0.45/a |
| 7 | 2-Cl, 3-Cl | $C_2H_5$ | 25 | 167–71 | |
| 8 | 4-$OCH_3$, 3-H | $CH_3$ | 19 | 136–40 | |
| 9 | 4-$C_6H_5$ | $CH_3$ | 28 | 177–79 | |
| 10 | 3-Cl, 4-Cl | $CH_3$ | 25 | 167–70 | |

We claim:

1. A substituted 6-amino-4H-pyran selected from the group consisting of

Methyl 6-amino-5-cyano-4-(2-trifluoromethyl-phenyl)-2-methyl-4H-pyran-3-carboxylate;

Methyl 6-amino-5-cyano-4-(2,3-dichloro-phenyl)-2-methyl-4H-pyran-3-carboxylate;

Methyl 6-amino-5-cyano-4-(4-trifluoromethyl-phenyl)-2-methyl-4H-pyran-3-carboxylate;

Methyl 6-amino-5-cyano-4-(4-chloro-phenyl)-2-methyl-4H-pyran-3-carboxylate;

Ethyl 6-amino-5-cyano-4-(2,3-dichloro-phenyl)-2-methyl-4H-pyran-3-carboxylate;

Methyl 6-amino-5-cyano-4-(4-methoxy-phenyl)-2-methyl-4H-pyran-3-carboxylate;

Methyl 6-amino-5-cyano-4-(4-phenyl-phenyl)-2-methyl-4H-pyran-3-carboxylate; and

Methyl 6-amino-5-cyano-4-(3,4-dichloro-phenyl)-2-methyl-4H-pyran-3-carboxylate.

2. A pharmaceutical composition which comprises an effective amount of a 6-amino-4H-pyran according to claim 1 and a formulation auxiliary.

3. A method of treating central nervous system disorders or a method of treating sickle cell anemia which comprises administering an effective amount of a 6-amino-4H-pyran of the formula

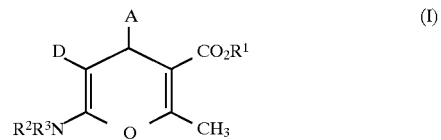

(I)

in which

A represents aryl having 6 to 10 carbon atoms or pyridyl, each of which is optionally substituted up to 3 times by identical or different substituents selected from the group consisting of nitro, cyano, phenyl, halogen trifluoromethyl, or straight-chain or branched alkylthio or alkoxy in each case having up to 6 carbon atoms, $R^1$ represents hydrogen or straight-chain or branched alkyl having up to 8 carbon atoms, $R^2$ and $R^3$ are identical or different and represent hydrogen or straight-chain or branched alkyl or acyl in each case having up to 6 carbon atoms, D represents cyano or nitro or a salt thereof to a host in need thereof.

4. The method according to claim 3, wherein

A represents phenyl, naphthyl or pyridyl, each of which is optionally substituted up to 3 times by identical or different substituents from the group consisting of nitro, cyano, fluorine, chlorine, bromine, iodine, phenyl, trifluoromethyl, straight-chain or branched alkylthio and alkoxy in each case having up to 4 carbon atoms.

$R^1$ represents hydrogen or straight-chain or branched alkyl having up to 6 carbon atoms, $R^2$ and $R^3$ are identical or different and represent hydrogen or straight-chain or branched alkyl or acyl in each case having up to 4 carbon atoms, D represents cyano or nitro, or a salt thereof.

5. The method according to claim 3, wherein

A represents phenyl or pyridyl, each of which is optionally substituted up to 2 times by identical or different substituents selected from the group consisting of nitro, cyano, fluorine, chlorine, bromine, iodine, trifluoromethyl, methoxy, phenyl and methylthio, D represents cyano, $R^1$ represents hydrogen or straight-chain or branched alkyl having up to 4 carbon atoms, $R^2$ and $R^3$ are identical or different and represent hydrogen or straight-chain or branched alkyl or acyl in each case having up to 3 carbon atoms, or a salt thereof.

6. The method according to claim 3, wherein the disorder is a degenerative central nervous system disorder.

7. The method according to claim 3, wherein the disorder is a dementia.

8. The method according to claim 3, wherein the disorder is a brain function disorder of old age.

9. The method according to claim 3, wherein the method is for the treatment of cerebral circulatory disorders.

* * * * *

UNITED STATES PATENT AND TRADEMARK OFFICE
CERTIFICATE OF CORRECTION

PATENT NO. : 5,874,462
DATED      : February 23, 1999
INVENTOR(S): Urbahns, et al.

It is certified that error appears in the above-identified patent and that said Letters Patent is hereby corrected as shown below:

| | |
|---|---|
| Title Page | OTHER PUBLICATIONS: Line 3 after " 793- " delete " 194 " and substitute -- 794 -- |
| Col. 6, line 31 | Delete " or " (first occurrence) |
| Col. 6, line 32 | Delete " or " and substitute -- and -- |

Signed and Sealed this

Twenty-seventh Day of July, 1999

Attest:

Q. TODD DICKINSON

*Attesting Officer*   *Acting Commissioner of Patents and Trademarks*